(12) United States Patent
Valenti et al.

(10) Patent No.: US 10,479,729 B2
(45) Date of Patent: *Nov. 19, 2019

(54) SHADED ZIRCONIA CERAMIC MATERIAL AND MACHINABLE SINTERED CERAMIC BODIES MADE THEREFROM

(71) Applicant: James R. Glidewell Dental Ceramics, Inc., Newport Beach, CA (US)

(72) Inventors: Thomas C. Valenti, Rancho Santa Margarita, CA (US); Kevin Michael Recor, Mission Viejo, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/895,516

(22) Filed: Feb. 13, 2018

(65) Prior Publication Data

US 2018/0237345 A1    Aug. 23, 2018

Related U.S. Application Data

(60) Provisional application No. 62/461,894, filed on Feb. 22, 2017.

(51) Int. Cl.
*C04B 35/486* (2006.01)
*A61C 13/083* (2006.01)
(Continued)

(52) U.S. Cl.
CPC ........ *C04B 35/488* (2013.01); *A61C 13/0022* (2013.01); *A61C 13/083* (2013.01); *A61K 6/024* (2013.01); *C01F 17/0075* (2013.01); *C01G 37/00* (2013.01); *C04B 35/486* (2013.01); *C01P 2002/52* (2013.01); *C01P 2002/54* (2013.01); *C01P 2006/60* (2013.01); *C01P 2006/62* (2013.01); *C01P 2006/63* (2013.01);
(Continued)

(58) Field of Classification Search
CPC . C04B 35/486; C04B 35/488; C04B 35/4885; A61K 6/024; A61C 13/83
See application file for complete search history.

(56) References Cited

U.S. PATENT DOCUMENTS

| 7,316,740 B2 | 1/2008 | Schweiger et al. |
| 7,497,983 B2 | 3/2009 | Khan et al. |

(Continued)

FOREIGN PATENT DOCUMENTS

| WO | 2015084931 A1 | 6/2015 |
| WO | 2016019114 A1 | 2/2016 |

*Primary Examiner* — Karl E Group
(74) *Attorney, Agent, or Firm* — Dianne Burkhard (57) ABSTRACT

Shaded, zirconia ceramic materials are disclosed that are suitable for use in dental applications. Ceramic bodies are made from a zirconia-containing ceramic material and a coloring composition comprising a terbium (Tb)-containing component and a chromium (Cr)-containing component as a coloring agent. The pre-shaded ceramic body is machinable into a dental restoration either as a bisque body or sintered body. A pre-shaded machinable sintered ceramic body may obviate the need for further processing steps, such as shading or sintering, and may be suitable for use in chair-side machining applications, such as in a dentist's office, significantly reducing the time to create a custom finished product.

20 Claims, 3 Drawing Sheets

(51) Int. Cl.
  *A61K 6/02*    (2006.01)
  *C04B 35/488*  (2006.01)
  *C01F 17/00*   (2006.01)
  *C01G 37/00*   (2006.01)
  *A61C 13/00*   (2006.01)

(52) U.S. Cl.
  CPC ...... *C01P 2006/64* (2013.01); *C01P 2006/80* (2013.01); *C04B 2235/3217* (2013.01); *C04B 2235/3224* (2013.01); *C04B 2235/3225* (2013.01); *C04B 2235/3232* (2013.01); *C04B 2235/3239* (2013.01); *C04B 2235/3241* (2013.01); *C04B 2235/3262* (2013.01); *C04B 2235/3275* (2013.01); *C04B 2235/3279* (2013.01); *C04B 2235/3281* (2013.01); *C04B 2235/3284* (2013.01); *C04B 2235/40* (2013.01); *C04B 2235/443* (2013.01); *C04B 2235/6562* (2013.01); *C04B 2235/6567* (2013.01); *C04B 2235/661* (2013.01); *C04B 2235/77* (2013.01); *C04B 2235/9661* (2013.01)

(56) References Cited

U.S. PATENT DOCUMENTS

| | | | |
|---|---|---|---|
| 8,034,264 | B2 | 10/2011 | Ritzberger et al. |
| 8,173,562 | B2 | 5/2012 | Höland et al. |
| 8,298,329 | B2 | 10/2012 | Knapp et al. |
| 9,095,403 | B2 | 8/2015 | Carden et al. |
| 9,365,459 | B2 | 6/2016 | Carden et al. |
| 9,428,422 | B2 | 8/2016 | Kawamura et al. |
| 9,434,651 | B2 | 9/2016 | Carden |
| D769,449 | S | 10/2016 | Leeson et al. |
| 9,505,662 | B2 | 11/2016 | Carden et al. |
| 9,512,317 | B2 | 12/2016 | Carden et al. |
| 2009/0115084 | A1 | 5/2009 | Moon |
| 2012/0139141 | A1 | 6/2012 | Khan et al. |
| 2015/0222212 | A1 | 8/2015 | Iwata |
| 2016/0038381 | A1 | 2/2016 | Jahns |
| 2017/0044068 | A1* | 2/2017 | Carden .................. A61K 6/024 |
| 2018/0235847 | A1* | 8/2018 | Balasubramanian .. A61K 6/024 |

* cited by examiner

SHADED ZIRCONIA CERAMIC MATERIAL AND MACHINABLE SINTERED CERAMIC BODIES MADE THEREFROM

This application claims the benefit of and priority to U.S. Provisional Patent Application No. 62/461,894, filed Feb. 22, 2017, the entirety of which application is incorporated herein by reference.

BACKGROUND

Methods for shading materials for use in dental restorations are known. Ceramic materials in the form of powder and partially sintered bodies may be predictably colorized to achieve a shade of natural or matching dentition in a completed, fully sintered, dental restoration.

In one method, coloring agents in the form of colorized dipping solutions penetrate porous ceramic structures that are milled from bisque, or partially sintered, ceramics. After milling and dipping in coloring solutions, the colorized ceramic bodies are sintered to full density, achieving a targeted shade in the final dental restoration.

Ceramic material may be colorized prior to forming the material into millable ceramic blanks. For example, coloring agents may be added during ceramic processing steps, or via fluidized bed reaction of unshaded powders, or by blending pre-shaded ceramic powders. Colorized ceramic materials formed into shaded ceramic blanks may be milled as pre-sintered bodies, and then fully sintered to form a dental appliance in a variety of target shades.

Coloring solutions containing terbium and chromium are known for use in dental applications in which pre-sintered or bisque zirconia ceramic bodies shaped as dental restorations are soaked for penetration by the coloring solution. The combination of iron, erbium, and/or cobalt, for colorizing dental ceramic materials is known in dental applications as providing a desirable shade match to natural dentition in comparison to some alternative dental ceramic coloring components.

Sintered, shaded blanks may be useful for preparing chairside dental applications by eliminating the lengthy sintering step utilized with traditional restorative dentistry techniques. The ability to mill sintered blocks allows the dentist to scan, mill, and seat a crown within a few hours. The consolidation of multiple dental visits (required for traditional techniques) to a chairside process is beneficial to both the dentist and patient. However, color uniformity throughout a mass and/or volume of a millable, sintered ceramic body used in chairside applications may not be achievable for all shades utilizing iron, erbium, and/or cobalt shading systems.

SUMMARY OF THE INVENTION

Shaded ceramic material, for use in making machinable sintered ceramic bodies, for use in dental applications, is disclosed. Machinable, sintered, ceramic bodies are made from zirconia-containing ceramic material and a coloring composition comprising terbium (Tb) and chromium (Cr) as a coloring agent. A pre-shaded, sintered ceramic body is machinable into a finished dental restoration, obviating further processing steps, such as shading or sintering. The machinable preform may be suitable for use in chair-side machining applications (for example, in a dentist's office), significantly reducing the time to create a custom finished product.

Sintered ceramic preforms are pre-shaded to match a multiplicity of targeted shades frequently selected for dental restorations. Pre-shaded ceramic materials, made according to the methods provided herein, have color uniformity throughout the mass and/or volume of the sintered body, overcoming limitations inherent in known colorization processes for dental ceramics. A method is provided for making shaded sintered bodies that have yellow to yellow/brown hues. The ceramic material is shaded with a coloring agent that comprises terbium and chromium ions, thereby eliminating reliance on iron-containing coloring agents commonly used to achieve similar shades. Coloring agents comprise a mass ratio of terbium ions to chromium ions in a range of approximately 93 Tb ions to 7 Cr ions to approximately 99.5 Tb to 0.5 Cr ions. In one embodiment, coloring agents may also include additional metal-containing components, including metal complexes and metal compounds, such as metallic salts of erbium, cobalt, or mixtures thereof.

Iron, if detectable, may be present in an amount of less than approximately 0.01 mass %, or for example, less than approximately 0.002 mass % as a contaminant in the raw material. Inconsistent colorization throughout the mass and/or volume of a sintered body may result with iron as a component of a coloring agent in some instances. When high concentrations of iron are included as a coloring agent, color or shade variations may appear in the internal mass and/or volume of the sintered ceramic body, which may be visibly different from the color and/or shade of the sintered body near the surface.

By materials and processes disclosed herein, shaded ceramic bodies comprising low or undetectable amounts of iron are formed that match the color of sintered ceramic restorations made from iron-containing ceramic materials. A comparison of color space values of shaded ceramic bodies disclosed herein and ceramic bodies colorized with iron-containing components, demonstrates $\Delta E$ of approximately 3 or less, 2.5 or less, or 2 or less, indicating color matching. Sintered bodies made from coloring agents that comprise metals and/or metal ions of Tb and Cr also have high flexural strength suitable for use in anterior and/or posterior dental applications, and uniform color throughout the mass and/or volume of a body. In one embodiment, sintered ceramic bodies have $L^*a^*b^*$ values in the following ranges when tested according to the methods described herein: $L^*$=approximately 50 to approximately 85; $a^*$=approximately −8 to approximately 8; and $b^*$=approximately −5 to approximately 35.

DETAILED DESCRIPTION

Shaded, sintered ceramic bodies disclosed herein, comprise a zirconia-containing ceramic material and a metal-containing component comprising terbium (Tb) and chromium (Cr) as a coloring agent. The ceramic bodies exemplified in FIG. 1a through FIG. 1d are suitable for use in chair-side dental applications requiring no further processing steps, such as shading or sintering, after the ceramic bodies are machined into dental restorations. The shaded, sintered ceramic bodies have uniform color throughout the internal mass and/or volume, and flexural strength suitable for use in anterior and posterior dental applications.

The ceramic body comprises ceramic materials including zirconia, yttria, and optionally, aluminum oxide, or other known oxides for use in ceramic materials, or mixtures thereof. Zirconia ceramic may comprise approximately 85% by weight to approximately 100% by weight of the ceramic material total weight. Zirconia ceramics may comprise zirconia, partially stabilized or stabilized zirconia, such as tetragonal or cubic zirconia, and mixtures thereof. The ceramic body may comprise approximately 0 mol % to approximately 1 mol % alumina. Yttria-stabilized and partially stabilized zirconia may comprise approximately 2 mol % to approximately 8 mol % yttria, or approximately 2.5 mol % to about approximately 7.5 mol % yttria, or approximately 2 mol % to approximately 7 mol % yttria, or approximately 3 mol % to about 6.5 mol % yttria, or approximately 3 mol % to about 6 mol % yttria, or approximately 4 to approximately 6 mol % yttria. Stabilized and partially stabilized zirconia materials suitable for use herein are commercially available, for example, through Tosoh, USA. Suitable methods for making dental ceramic materials may be found in commonly owned U.S. Pat. No. 8,298,329, which is incorporated by reference, herein, in its entirety.

In addition to Tb and Cr, coloring agents may include other metal-containing components, including metallic compounds and metallic complexes having one or more metallic elements of transition metals from groups 3-14 on the periodic table of elements, rare earth metals, or mixtures of transition metals and rare earth metals. A coloring agent may further comprise one or more metal-containing components having a metal or metal ion including, but not limited to, Er, Co, Mn, Pr, V, Ti, Ni, Cu and Zn, to provide a coloring effect. Metallic oxides, or metallic salts containing anions such as $Cl^-$, $SO_4^{2-}$, $SO_3^{2-}$, $Br^-$, $F^-$, $NO_2^-$, and $NO_3^-$, may be suitable for use herein. A total approximate amount of metal added as a coloring agent in the shaded ceramic powder or sintered body may comprise 0.03 mass % to 2 mass % measured as metal ions, or 0.027 mass % to 1.6 mass %, or 0.02 mass % to 1.4 mass %, measured as metal ions.

Metal-containing components containing iron or iron-containing compounds may be absent, or below detectable limits in the shaded ceramic powder or sintered body. Iron may be present, for example, as iron oxide, in an amount between approximately 0 mass % and 0.002 mass %-containing component (measured as iron ions). In some embodiments, an iron-containing component may be present in an amount less than approximately 0.01 mass % (measured as iron ions).

The coloring agent may comprise a mass ratio of Tb ions to Cr ions is in a range of approximately 93 Tb ions to 7 Cr ions (i.e., 93:7 Tb:Cr) to approximately 99.5 Tb ions to 0.5 Cr ions (i.e., 99.5:0.5 Tb:Cr). Alternatively, the mass ratio of Tb ions to Cr ions is in a range of approximately 94:6 Tb:Cr to approximately 99:1 Tb:Cr, or approximately 95.1:4.9 Tb:Cr to approximately 99.1:0.9 Tb:Cr. Alternatively, the mass ratio of Tb ions to Cr ions is in a range of approximately 96:4 Tb:Cr to approximately 98:2 Tb:Cr, or approximately 96.7:3.3 Tb:Cr to approximately 98.6:1.4 Tb:Cr. Terbium-containing components may include, but are not limited to terbium (III) chloride, terbium (III) acetate and terbium (III) nitrate. Chromium-containing components may include, but are not limited to, chromium (III) chloride, chromium (III) acetate and chromium (III) nitrate.

A total combined mass % Tb and Cr ions in the shaded ceramic powder may be in the range of approximately 0.002 mass % to approximately 0.65 mass % Tb and Cr ions, combined, as a coloring agent. In one embodiment, the ceramic material comprises approximately 0.002 mass % to 0.4 mass %, or approximately 0.002 mass % to 0.3 mass %, or approximately 0.002 mass % to 0.2 mass %, total combined Tb and Cr ions, as a coloring agent. Tb ions may comprise approximately 0.002 mass % to approximately 0.63 mass %, or 0.002 mass % to approximately 0.62 mass %, or approximately 0.002 mass % to 0.3 mass %, or approximately 0.0047 mass % to approximately 0.278 mass %, of the ceramic material. Cr ions may comprise approximately 0.00006 mass % to 0.018 mass %, or approximately 0.000006 mass % to 0.01 mass %, or approximately 00014 mass % to 0.0082 mass %, of the ceramic material.

In one embodiment, shaded ceramic material may further comprise an erbium (Er)-containing component (measured as mass % Er ions) in a range of approximately 0.008 mass % to approximately 1.45 mass % Er ions, as a coloring agent, or, alternatively, approximately 0.0244 mass % to 0.975 mass % Er ions, or approximately 0.02 mass % to 1.5 mass % Er ions, as a coloring agent. Optionally, shaded ceramic material may comprise a cobalt-containing component (measured as mass % Co ions) in a range of approximately 0 mass % to 0.009 mass %, or approximately 0 mass % to 0.0085 mass %, or approximately 0 mass % to approximately 0.0068 mass %, as a coloring agent.

Coloring agents may be incorporated with the ceramic material during formation of the ceramic powder or after formation of the ceramic powder, before formation of the ceramic green body, or after formation of the green body. Techniques for incorporating metal ions as coloring agents into ceramic powder include, but are not limited to, mechanical mixing, fluidized bed mixing, V-blending with agitator bar, colloidal mixing, and mixing pre-doped powders. For example, coloring solutions that contain coloring agents may be mixed with ceramic materials in the form of ceramic slurries, during slip casting processes, prior to casting into a mold to form a ceramic block. Methods suitable for use herein also include, but are not limited to methods disclosed in U.S. Pat. No. 9,505,662, that is incorporated by reference herein, in its entirety. In a further method, colored ceramic powder first prepared, for example, by colloidal processes may be subsequently formed into green state ceramic bodies by isostatic or biaxial press manufacturing processes as described in commonly owned U.S. Pat. No. 9,512,317, also incorporated by reference herein in its entirety. Coloring agents comprising metallic salts in the form of coloring liquids may be mixed directly with unshaded or white ceramic powders, prior to pressing into blocks. Further, colored ceramic powders may be blended with other colored or uncolored ceramic powders to achieve a shaded ceramic material suitable for use in dental applications. Optionally, intermediate preform shapes comprising porous ceramic materials may be shaded, for example, by dipping into coloring liquids prior to sintering to full density.

Shaded ceramic powders may be shaped to have substantially the same geometry as the final machinable, sintered preform, and may be enlarged to accommodate shrinkage upon sintering. Processes for making the shaped ceramic body may include injection molding ceramic powder, or milling, or grinding unsintered or partially sintered ceramic blocks. Shaded ceramic powders made into blocks by molding and pressing, for example, such as by biaxial or isostatic pressing, may further comprise binders and processing aids. Alternatively, ceramic powders may be processed into blocks by slip casting processes, such as those described in commonly owned U.S. Patent Publication No. 2009/0115084, and U.S. Pat. Nos. 9,365,459 and 9,434,651, or pressing processes described in commonly owned U.S. Pat. No. 9,512,317, all of which are incorporated herein, by reference, in their entirety. Shaded slip-cast and pressed ceramic block may be pre-sintered to a bisque-stage, and then may be cut or milled into any dental shape or form, before heating to form a fully sintered the ceramic body. Shaded ceramic powders also may be shaped into porous intermediate, shaped ceramic preforms that may be sintered to approximately full theoretical density, to form the machinable sintered ceramic bodies. The sintered ceramic body has a size and shape that accommodates most custom restoration designs. The preform body portion of the ceramic body, within which the restoration design is nested for shaping by automated processes, may have a circular or a non-circular cross-sectional geometry, or an irregular shaped cross-sectional geometry.

To enhance color uniformity throughout the mass and/or volume of a sintered body, a sintering process is disclosed that may contribute to color uniformity for sintered ceramic bodies having thicknesses greater than approximately 6 mm. The process comprises a sintering step in which the oven temperature (in which a green or bisque state ceramic body is placed) is slowly increased from a first temperature to a second temperature, wherein each of the first and second temperatures are in the range of approximately 950° C. to approximately 1450° C., and the difference between the first and second temperature is at least 50° C., or at least 100° C. For example, the first temperature is in the range of about 950° C. to about 1400° C., and the second temperature is in the range of about 1000° C. to about 1450° C. In one embodiment, for example, the oven temperature is slowly increased between a first temperature of approximately 1050° C. and a second temperature of approximately 1350° C. The rate at which the oven temperature is increased between the two temperatures within this range may be approximately 0.01° C. per minute (° C./min.) to approximately 5° C./min. or approximately 0.02° C. per minute (° C./min.) to approximately 4° C./min., or approximately 0.03° C. per minute (° C./min.) to approximately 3° C./min. Alternatively, the rate at which the oven temperature is increased from the first temperature to the second temperature is in the range of approximately 0.1° C. per minute to approximately 0.5° C./min., or approximately 0.1° C. per minute to approximately 0.3° C./min.

The first temperature, the second temperature or both the first and second temperatures may be held, for example, from approximately 0 minutes to about 12 hours. In other embodiments, the sintering profile comprising a ramp rate between approximately 0.01° C. per minute (° C./min.) to approximately 5° C./min., may further comprise one or more dwell times between the first and second temperatures; in one embodiment, the sintering profile may comprise a dwell time that is greater than 90 minutes.

In another embodiment, the oven temperature is further increased in a subsequent step, for example, from the second temperature to a third or subsequent final peak temperature that is in the range of approximately 1300° C. to approximately 1700° C. The third temperature or subsequent final peak temperature may be held, for example, between approximately 0 minutes and approximately 24 hours, or approximately 2 hours and approximately 12 hours.

Commonly known ramp rates may be used to reach the first temperature for example, when heating the oven from an ambient temperature to the first temperature. Suitable known ramp rates may include, but are not limited to, those in the range of approximately 0.5° C./minute to approximately 100° C./min., or approximately 8° C./min to approximately 12° C./min. Ramp rates in this range may also be suitable to increase the oven temperature from the second temperature to a third, or subsequent final peak, oven temperature.

As exemplified in FIGS. 1A, 1B, 1C, and 1D, a machinable sintered ceramic body 100 may comprise a cylindrical preform body 101 from which a restoration design is shaped, and a support structure 102, or stem, that projects from the preform body for attachment to a mandrel or milling machine, with or without an attachment portion 103. Processes for shaping a fully sintered preform body portion into a dental restoration include, but are not limited to, slicing, milling and/or grinding. An exemplary embodiment of a sintered body shape is disclosed in commonly owned U.S. Pat. No. D769, 449, filed Aug. 3, 2015, which is incorporated herein, by reference, in its entirety, and commonly owned U.S. patent application Ser. No. 15/222,212, filed Jul. 28, 2016, also incorporated by reference in its entirety, herein. The term "fully sintered" ceramic body refers to ceramic bodies having densities that approximate the theoretical density (g/cm$^3$) of a fully sintered body (unless otherwise stated), which for purposes herein, a fully sintered zirconia body is assumed to be 6.08 g/cm$^3$.

A dental restoration design 107 fits within a computer model of the fully sintered preform body 101, and the ceramic restoration is milled to actual size because the ceramic body portion is fully sintered prior to machining. The preform body portion may be in the shape of a block or cube, cylinder, ellipsoid cylinder, a polyhedron, curved polyhedron, a cylinder with flattened surfaces, a cube with rounded edges, and the like. A center cross-section within the center portion 108 may intersect line Z-Z' of the sintered body 100, penetrating the sintered internal mass. In one embodiment, a circular center cross-section of the body portion 101 of FIG. 1a comprises a portion taken approximately equidistance from opposing body ends (104, 105) and passes approximately through line Z-Z'. A cross-sectional dimension of diameter, length, width and/or height of the cross-section may be between about 6 mm and 25 mm, or greater than approximately 6 mm, or greater than approximately 7 mm, or greater than approximately 8 mm, or greater than approximately 10 mm, or greater than approximately 12 mm, or greater than approximately 15 mm.

Sintered bodies have uniform color throughout a center cross-section of the internal mass and flexural strength suitable for use in anterior and posterior dental applications. Shaded sintered bodies may have CIE L*a*b* color space values in the following ranges when tested according to the methods described herein: L* value is approximately 50 to approximately 85, or approximately 60 to approximately 80, or approximately 67 to approximately 75; a* value is approximately −8 to approximately 8, or approximately −5 to approximately 5, or approximately −4 to approximately 3, or approximately −2 to approximately 5; and b* value is approximately −5 to approximately 35, or approximately −5 to approximately 25, or approximately 0 to approximately 25.

Flexural strength values greater than approximately 500 MPa may be achieved in the shaded sintered bodies, when tested according to ISO 6872:2015. A shaded sintered ceramic body may have a flexural strength greater than approximately 800 MPa, or greater than approximately 900 MPa, or greater than 1000 MPa.

In one embodiment, sintered machinable ceramic bodies comprise Tb and Cr in a mass ratio of approximately 93:7 Tb:Cr (measured as metallic ions) to about 99.5:0.5 Tb:Cr measured as metal ions, and an Fe-containing component that is less than about 0.01 mass % (measured as Fe ions). Sintered bodies containing Tb and Cr, and less than about 0.01 mass % Fe may be prepared having similar CIF L*a*b* values (e.g., having a ΔE of approximately 2.5 or less) as sintered bodies incorporating greater than 0.01 mass % iron (measured as Fe ions) as a coloring agent. Thus, a color match may be achieved between traditional ceramic bodies having iron-containing coloring agents and ceramic bodies described herein comprising Tb- and Cr-containing coloring agents.

In another embodiment, zirconia ceramic bodies may comprise less than or equal to approximately 0.1 mass % of an iron-containing component (measured as Fe ions), and further comprise Tb- and Cr-containing components (measured as Tb ions and Cr ions) in a ratio of Tb:Cr as described herein, for dark shaded bodies requiring high concentrations of coloring agents. For example, darker shades of ceramic materials suitable for use in dental applications may be produced by the combination of metal-containing components comprising Fe in an amount of about 0.01 mass % to 0.1 mass % (measured as Fe ions) in addition to Tb- and Cr-containing components (in the ratios described) herein, where color uniformity may be unachievable by Fe-containing coloring agents alone in sintered bodies having a diameter or width greater than, for example, approximately 6 mm, or greater than approximately 8 mm. In other embodiments, shaded zirconia ceramic materials may comprise less than or equal to approximately 0.08 mass %, or less than or equal to approximately 0.07 mass %, of an iron-containing component (measured mass % Fe-ions), and further comprise Tb- and Cr-containing components.

In another embodiment, a machinable sintered ceramic body comprises 3 mol % yttria to 6 mol % yttria-stabilized zirconia, and approximately 0.027 mass % to approximately 1.6 mass % of metal-containing components measured as metal ions as a coloring agent. The sintered body comprises approximately 0.008 mass % to approximately 0.14 mass % Tb in a mass ratio of Tb to Cr, measured as metal ions, that is between approximately 96.7:3.3 and approximately 98.6:1.4. The sintered ceramic body is uniformly shaded throughout a center cross-sectional geometry, wherein the smallest dimension of the sintered preform body (i.e., length, width, or height), is greater than or equal to approximately 7 mm. When measured for CIE L*a*b* color space, the sintered ceramic body, L* is in the range of approximately 60 to approximately 80; a* is in the range of approximately −2 to approximately 5; and b* is in the range of approximately 0 to approximately 25, when measured according to the methods provided herein for measuring color space.

Figure 2:
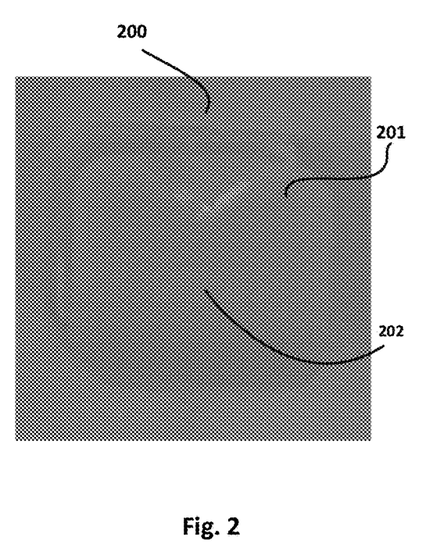
FIG. 2. A cross section of the internal mass of a sintered ceramic body comprising a mixture of terbium and chromium according to one embodiment.
Figure 3:
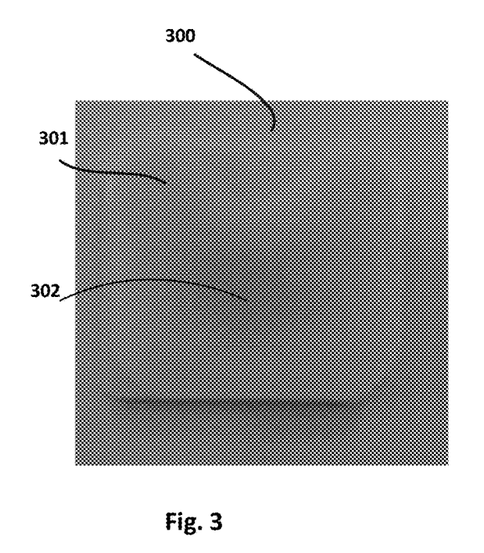
FIG. 3. A cross section of the internal mass of sintered ceramic body containing an iron-containing material in which color uniformity is not achieved.
Figure 4:
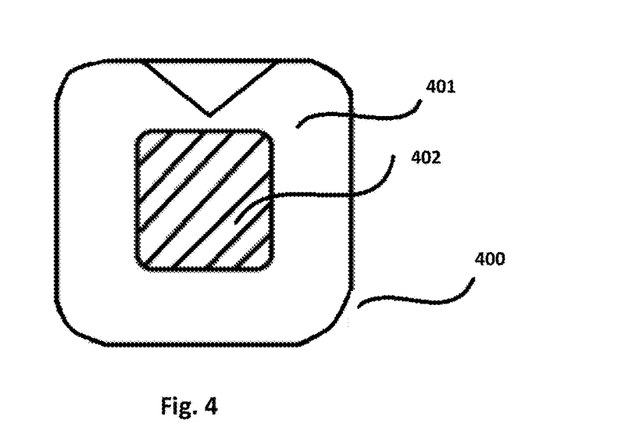
FIG. 4. An illustrated representation of a cross section of an internal mass of a sintered body in which color uniformity is not achieved.

Uniform color consistency throughout a ceramic body may be determined by measuring CIE L*a*b* values at a cross-sectional surface center (e.g., 202, 302, 402) and perimeter (e.g., 201, 301, 401) of the same ceramic body, measured and calculated by the methods reported herein. An exterior surface also may be compared to the cross-sectional center i.e., intersecting Z'-Z) to show color consistency throughout a ceramic body. A sintered body having a cross-sectional dimension suitable for milling a dental restoration (e.g., a minimum dimension greater than 6 mm), may have a ΔE of approximately 5 or less, indicating fair color consistency throughout the ceramic body. In other embodiments, a sintered ceramic body having uniform color consistency may have a ΔE that is approximately 4 or less, or approximately 3 or less, or approximately 2 or less, or approximately 1 or less, or approximately 0.6 or less, or approximately 0.5 or less, when comparing cross-sectional center and perimeter portions.

Dental restorations formable from the preforms disclosed herein include, but are not limited to, crowns, inlays, and onlays.

Test Method

Color Space (CIE L*a*b*) Test

Zirconia materials were measured for color space according to CIE L*a*b* (International Commission on Illumination, measuring two polar axes for color, 'a' and 'b', and value (lightness, L)) values using a Konica Minolta Spectrometer with a D65 light source.

27 mm×27 mm sintered test wafers were cut from pre-sintered bisque blocks. The targeted final thickness of the test wafers after sintering was 1.0 mm. Therefore, the starting thickness for each wafer was calculated based on the targeted final thickness taking into consideration the enlargement factor (EF) as follows:

Final thickness×(EF)=bisque wafer thickness.

To measure color equivalence between two different ceramic bodies, the Konica Minolta Spectrometer was set on reflectance mode, the measurement surface of the sintered block was placed flush against an 11 mm target aperture, and the L*a*b* values of the samples were measured.

These values were referenced to materials made from traditional processes. Color equivalence is indicated if a comparison of ceramic samples made by the methods described herein and traditional methods have a ΔE of less than approximately 3 or less, approximately 2.5 or less, or approximately 2 or less for good color equivalence, and a ΔE between about 3 and 5 indicated fair color equivalence.

ΔE values were calculated using the following equation:

$$\Delta E = \sqrt{(L1-L2)^2 + (a1-a2)^2 + (b1-b2)^2}$$

Flexural Strength

Samples for three-point bend strength (flexural strength) testing were milled and prepared according to ISO 6872:2015 for the preparation of strength testing for dental ceramic materials. Results are provided in MPa. Flexural strength bars of ceramic materials were milled out of a bisqued block then ground flat with 1200 grit SiC polishing paper until visually free of defects. The bisqued bars were ground to a thickness corresponding to approximately 1.68× 25×4 mm3 after sintering. After sintering, the central region of both the tensile and compressive surfaces were visually inspected for defects by optical microscope. The side with the fewest observed defects was chosen as the side broken in tension (facedown in the test fixture). Flexural testing was performed on a Shimadzu EZ-Test universal testing machine with a custom-built three-point bend fixture according to ISO 6872:2015. The bars were aligned on the two rollers using a metal guide. Sample sets contained at least 10 bars.

Flexural strengths were calculated via the measured breaking load and measured dimensions.

EXAMPLES

Example 1

Shaded zirconia ceramic blocks were sintered to full theoretical density and testing for color properties.

Pressable, zirconia ceramic powder was obtained that comprised 3 mol % yttria-stabilized zirconia. The zirconia ceramic powder was doped with a coloring composition comprising terbium-, chromium-, erbium- and cobalt-containing compositions as a coloring agent. The ceramic powder comprised approximately 0.34 mass % of a mixture of terbium (III) nitrate hexahydrate and chromium (III) nitrate nonahydrate per gram of zirconia ceramic powder. The ratio of terbium ion to chromium ion was approximately 95:5 Tb:Cr by mass.

Figure 1A:
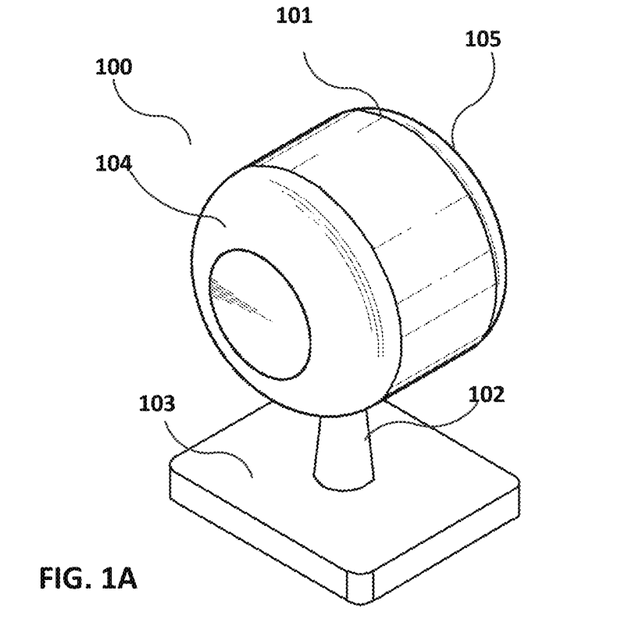
FIG. 1A. A perspective view of an illustration of one embodiment of a sintered ceramic shape suitable for use in a chairside milling process.
Figure 1B:
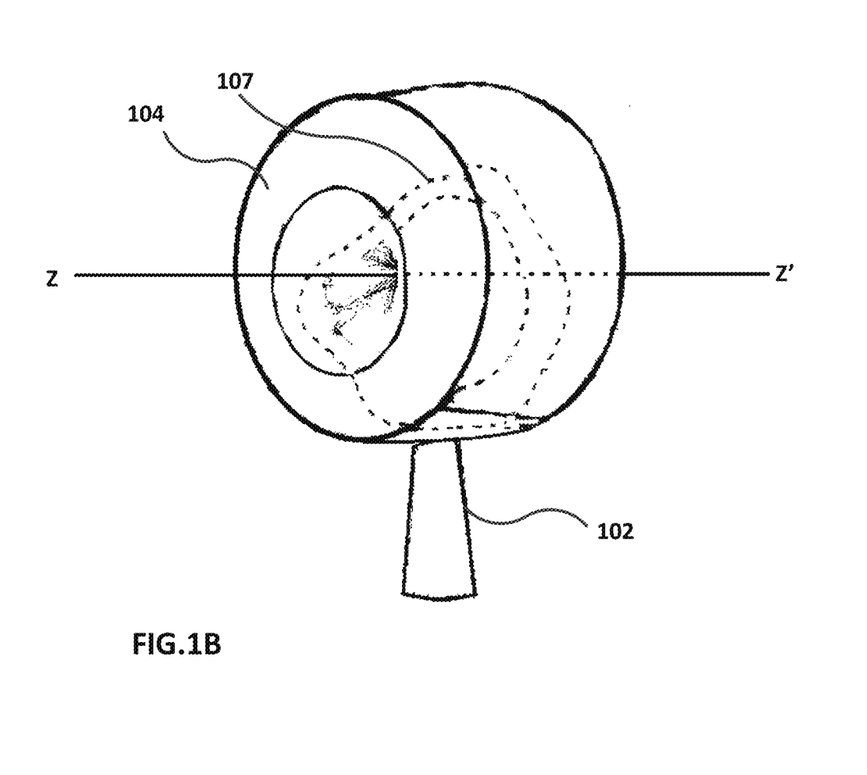
FIG. 1B. A perspective view of an illustration of a sintered ceramic body and a nested dental restoration.
Figure 1C:
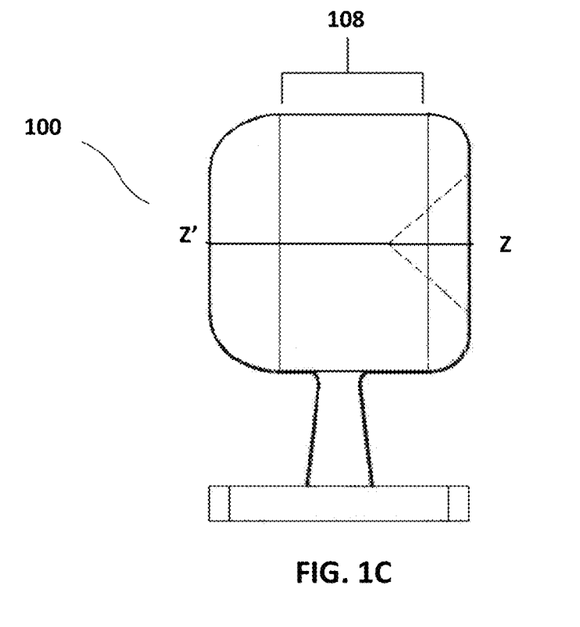
FIG. 1C. A side view illustration of a sintered ceramic body according to one embodiment.
Figure 1D:
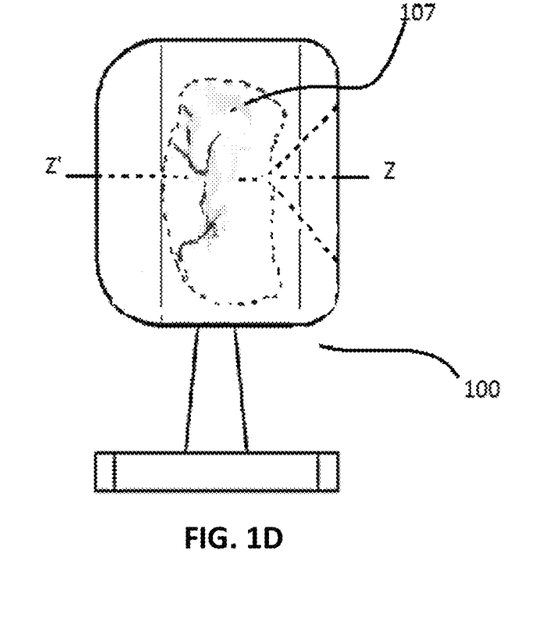
FIG. 1D A side view illustration of a sintered ceramic body and a nested dental restoration according to one embodiment.

The shaded powders were pressed into blocks measuring approximately 98 mm diameter×20 mm height by isostatic pressing. Ceramic shapes similar to FIG. 1 were milled from these blocks and sintered to approximately full theoretical densities (approximately 6.08 g/cm3) according to the following sintering profile: milled blocks were placed in a sintering oven that was heated to approximately 1050° C. at a rate of 10° C./min, with a hold time of 0 minutes. The oven temperature was increased from 1050° C. to approximately 1350° C. at a ramp rate of approximately 0.2° C./min, with a hold time of 0 minutes. The oven temperature was increased from approximately 1350° C. to approximately 1550° C. at a rate of 10° C./min., and the temperature was held at approximately 1550° C. for about 6 hours, and then cooled.

The sintered ceramic bodies had a cylindrical shape, having a circular cross-sectional geometry measuring approximately 14 mm in diameter, and having a cylindrical length of approximately 12 mm. Cross-sections of each of the fully sintered ceramic bodies were obtained approximately equidistance between opposing cylindrical end, and approximately parallel to Z-Z'. Visual inspection of cross-sections from each sintered ceramic body showed consistent yellow shading through the thicknesses of the fully sintered blocks as shown in FIG. 2.

Examples 2-12

Shaded, sintered ceramic bodies were prepared from 4 mol % yttria-stabilized zirconia powder that was colorized with a mixture of metal-containing components of terbium and chromium as coloring agents. The shaded, sintered ceramic bodies were compared to shaded, sintered ceramic bodies made from ceramic powder comprising an iron-containing component as a coloring agent.

Ceramic powders were prepared in multiple shades according to Table 1, substantially according to the methods of Example 1. For each shade, a mixture of metal-containing components comprising Tb and Cr ions was provided having a metal ion ratio of approximately 94 to 6 of Tb to Cr, at multiple concentrations. For a given shade, a matching (color equivalent) ceramic material incorporating iron-containing components as a coloring agent was prepared that had a greater total metal ion concentration than the shade-equivalent ceramic materials shaded with a mixture of Tb- and Cr-containing coloring agents.

For determination of color matching between iron-containing ceramic materials and terbium/chromium-containing ceramic materials, color space analyses were performed using a Konica Minolta Spectrometer (11 mm aperture). Shaded ceramic powders of Table 1 were isostatically pressed, and pre-sintered into blocks of approximately 27 mm×27 mm, according to the Color Space (CIE L*a*b*) Test Method describe above. Wafers were cut from pre-sintered bisque blocks to a targeted post-sintering thickness of approximately 1 mm, and then sintered to form the sintered zirconia test wafers. Sintered zirconia wafers colored with iron-containing components were color matched to sintered zirconia wafers colored with terbium and chromium-containing components, as provided in Table 2. A comparison of CIE L*a*b* color space values (obtained using a Konica Minolta Spectrometer) between iron-containing sintered ceramic wafers and terbium and chromium-containing sintered ceramic wafers indicated good color matching (equivalency) between A and B samples for each Example, as indicated by ΔE of less than about 2.2, as reported in Table 2.

For an analysis of shade uniformity through a machinable sintered body, shaded ceramic powders of Table 1 were shaped into cylindrical bodies having a circular cross-sectional geometry measuring approximately 14 mm in diameter, and having a cylindrical length of approximately 12 mm, as described in Example 1. The cylindrical bodies were sintered according to the sintering profile of Example 1. A center cross-sectional sample of each Example was obtained 200, as exemplified in FIG. 2. The center cross-section was taken through the internal mass, approximately intersecting the diameters of each circular end and Z-Z'.

Color uniformity of the cross-sectional samples was ascertained by visual inspection of the cross-sectional surface area with the unaided eye of a trained technician, and reported in Table 1 (e.g., 'good', 'fair', 'poor' or 'extremely poor'). Visual inspection of cross-sectional samples showed consistent yellow shading through the thicknesses of the fully sintered bodies for Examples comprising terbium and chromium. As exemplified in FIG. 2, uniform yellow-brown color extended throughout the cross-sectional samples of sintered bodies 200, from the perimeter 201 to the center of the masses 202 of the Tb/Cr-containing sintered bodies. Iron-containing sintered bodies having about 0.07 mass % or less Fe (measured as mass % Fe ions), also yielded a color uniformity of 'good'.

Analysis of center cross-sections 300 taken from iron-containing samples of Examples 6(A) through 10(A), showed inconsistencies in color uniformity across the cross-sectional surface of each sample. Example 6(A) had slight yellow-brown shade inconsistency between the sample edge to the sample center, yielding a color uniformity result of 'fair' upon visual analysis by the unaided eye.

For Examples 7(A), 8(A), 9(A) and 10(A), lighter colors of yellow to yellow-brown 301 and darker colors of blue/gray to black 302 were observed, as shown in FIG. 3. As illustrated in FIG. 4, cross-sectional samples 400 having inconsistent colorization had a perimeter 401 of yellow to yellow-brown color extending about 1 mm to 3 mm from the sample edge toward the center of the sintered mass. The color of the center portion 402 of the cross section was blue/gray-black for Examples 7(A), 8(A), 9(A) and 10(A). Examples 7(A) and 8(A) had color uniformity results of 'poor' where color varied from yellow at the perimeter to bluish-gray at the center, as detectable by the unaided eye. Examples 9(A) and 10(A) yielded a color uniformity result of 'extremely poor', where samples had color variations of yellow/yellow-brown at the perimeter and dark blue, gray and/or black colors in center of the cross-sectional samples.

TABLE 1

Comparison of Sintered Zirconia Bodies Shaded With Iron-Containing Component (A) And Sintered Zirconia Bodies Shaded with Tb and Cr Components (B). Examples 2-12 Formulations

| | Examples A (Fe) | | | | Examples B (Tb/Cr) | | | |
|---|---|---|---|---|---|---|---|---|
| Example # | % Zpex® 4 yellow powder | Fe ions (mass %) | Fe Color Uniformity | ΔE (between center and perimeter) | Tb ions (mass %) | Cr ions (mass %) | Tb/Cr Color Uniformity | ΔE (between center and perimeter) |
| 2 (A); (B) | 10 | 0.017 | Good | — | 0.0047 | 0.00014 | Good | — |
| 3 (A); (B) | 22 | 0.038 | Good | 1.2 | 0.014 | 0.00041 | Good | 0.6 |
| 4 (A); (B) | 30 | 0.052 | Good | — | 0.023 | 0.00066 | Good | — |
| 5 (A); (B) | 40 | 0.07 | Good | — | 0.036 | 0.00104 | Good | — |
| 6 (A); (B) | 49 | 0.086 | Fair | 2.8 | 0.049 | 0.00146 | Good | 0.3 |
| 7 (A); (B) | 60 | 0.105 | Poor | 9.5 | 0.07 | 0.00205 | Good | 0.5 |
| 8 (A); (B) | 70 | 0.122 | Poor | 10.6 | 0.091 | 0.00268 | Good | 0.5 |
| 9 (A); (B) | 77.5 | 0.136 | Extremely Poor | 20.6 | 0.109 | 0.0032 | Good | 0.6 |
| 10 (A); (B) | 90 | 0.157 | Extremely poor | — | 0.142 | 0.00418 | Good | — |
| 11 | NA | N/A | N/A | N/A | 0.278 | 0.0082 | Fair | 3.5 |
| 12 | NA | N/A | N/A | N/A | 0.62 | 0.018 | Fair | 4.7 |

TABLE 2

Color Match Comparison Between Iron-Containing and Tb/Cr Containing Sintered, Shaded Zirconia Ceramic Bodies.

| Example # | ΔE -between Examples A and B |
|---|---|
| 3 (A); (B) | 1.09 |
| 4 (A); (B) | 0.75 |
| 5 (A); (B) | 1.62 |
| 6 (A); (B) | 2.03 |
| 7 (A); (B) | 1.9 |
| 8 (A); (B) | 1.06 |
| 9 (A); (B) | 2.17 |

Color or shade analyses using a Vita Easyshade® Advance 4.0 Digital Shade Matching System device were performed on the cross-sectional samples of sintered cylindrical bodies to analyze uniformity between the sample center and perimeter as measured. ΔE was calculated as the difference between CIE L*a*b* values (by the calculation provided above) at the cross-sectional sample perimeter (e.g., 401) and the cross-sectional sample center (e.g., 402), and reported in Table 1.

Color or shade analysis results by the Vita Easyshade® shade matching system corresponded to the visual color uniformity analysis results (both reported in Table 1), where samples having a visual color uniformity result of 'good', also had ΔE of less than 2. The ΔE of less than 2 indicated good color equivalence of the perimeter and center. The iron-containing sample having a 'fair' color uniformity value had a ΔE of less than 3 (Example 6 (A) having ΔE of 2.8). Iron-containing samples having visually ascertainable "poor" and "extremely" poor color uniformity results had ΔE values greater than 9 (e.g., Examples 7A, 8A, and 9A.) In contrast, color-matched Examples 7B, 8B, and 9B, each had a ΔE less than or equal to 0.6, indicating "good" color equivalence, and therefore, color uniformity, between the perimeter and center of the cross-sectional samples.

Colored ceramic bodies of Examples 11 and 12 (containing terbium- and chromium-containing coloring agents) were each analyzed for color uniformity between perimeters and centers of the cross-sectional samples. Color uniformity was measured by the method described herein for Color Space (CIE L*a*b*) Test using a Konica Minolta Spectrometer, except that the measurement surface of the sintered block was placed flush against a 3 mm target aperture. Examples 11 and 12 each had a ΔE greater than 3 but less than 5, indicating that fair color uniformity was achieved throughout the sintered body.

We claim:

1. A sintered ceramic body suitable for use in dental restoration applications comprising:
   a. a ceramic material that comprises zirconia and
   b. a coloring agent comprising 0.002 mass % to 0.65 mass % of terbium (Tb) and chromium (Cr) combined, measured as metal ions,
   wherein the mass ratio of Tb to Cr, measured as metal ions, is in the range of approximately 93:7 Tb:Cr to approximately 99.5:0.5 Tb:Cr.

2. The sintered ceramic body of claim 1, wherein the mass ratio of Tb to Cr, measured as metal ions, is in the range of approximately 94:6 Tb:Cr to approximately 99:1 Tb:Cr.

3. The sintered ceramic body of claim 1, wherein the coloring agent further comprises at least one element selected from Er, Co, Mn, Pr, V, Ti, Ni, Cu and Zn.

4. The sintered ceramic body of claim 1, wherein at least one coloring agent further comprises at least one element selected from Er, Co, Mn, and Pr.

5. The sintered ceramic body of claim 1, comprising between 0.01 mass % and 0.1 mass % Fe.

6. The sintered ceramic body of claim 1, comprising between 0 mass % and 0.002 mass % Fe ions.

7. The sintered body of claim 1, having a center cross-sectional geometry that is at least 6 mm.

8. The sintered body of claim 7, having a CIE L*a*b* ΔE of less than 5 between a cross-sectional center and a perimeter of the sintered ceramic body.

9. The sintered body of claim 7, having a CIE L*a*b* ΔE of less than 3 between a cross-sectional center and a perimeter of the sintered ceramic body.

10. The sintered ceramic body of claim 1, wherein the coloring agent comprises
    a. 0.002 mass % to 0.3 mass % Tb, measured as Tb ions,
    b. 0.000006 mass % to 0.01 mass % Cr, measured as Cr ions,
    c. 0.02 mass % to 1.5 mass % Er, measured as Er ions, and
    d. 0 mass % to 0.009 mass % Co, measured as Co ions.

11. The sintered ceramic body of claim 1 wherein zirconia comprises between 85 wt % to approximately 100 wt % of the ceramic material.

12. The sintered ceramic body of claim 1, wherein the ceramic material comprises yttria-stabilized zirconia comprising from 2 mol % to 7 mol % yttria, and 0 mol % to 1 mol % alumina.

13. A ceramic powder suitable for use in dental restoration applications that comprises
   a. a ceramic material comprising an yttria-stabilized zirconia that comprises from 2 mol % to 7 mol % yttria, and
   b. a coloring agent comprising 0.002 mass % to 0.65 mass % Tb and Cr combined, measured as metal ions,
      wherein a mass ratio of Tb ions to Cr ions is in a range of approximately 93:7 Tb:Cr to 99.5:0.5 Tb:Cr, and
   c. optionally, a binder.

14. The ceramic powder of claim 13, comprising 0.002 mass % to 0.3 mass % Tb and Cr combined, measured as metal ions.

15. The ceramic powder of claim 13, wherein the mass ratio of Tb to Cr, measured as metal ions, is in the range of approximately 94:6 Tb:Cr to approximately 99:1 Tb:Cr.

16. The ceramic powder of claim 13, wherein the coloring agent further comprises at least one element selected from Er, Co, Mn, Pr, V, Ti, Ni, Cu and Zn.

17. A millable, pre-sintered ceramic body for use in making dental restorations comprising:
   a. a ceramic material comprising an yttria-stabilized zirconia having from 2 mol % to 7 mol % yttria,
   b. optionally comprising alumina, which if present comprises between 0 mol % and 1 mol %, and
   c. a coloring agent comprising 0.03 mass % to 2 mass % of metal-containing components measured as metal ions,
wherein the coloring agent comprises terbium (Tb) and chromium (Cr) which are present in a mass ratio in a range of 93:7 Tb:Cr to 99.5:0.5 Tb:Cr, and
wherein Tb comprises 0.002 mass % to 0.65 mass %.

18. The millable, pre-sintered ceramic body of claim 17, wherein the coloring agent further comprises at least one metal-containing component having an element selected from Er, Co, Mn, Pr, V, Ti, Ni, Cu and Zn.

19. The millable, pre-sintered ceramic body of claim 17, wherein the coloring agent comprises terbium (Tb) and chromium (Cr) which are present in a mass ratio in a range of 94:6 Tb:Cr to 99:1 Tb:Cr.

20. The millable, pre-sintered ceramic body of claim 17, wherein Tb comprises 0.002 mass % to 0.3 mass %.

* * * * *